United States Patent
Park et al.

(10) Patent No.: US 10,132,730 B2
(45) Date of Patent: Nov. 20, 2018

(54) APPARATUS FOR PREPARING CELL-DERIVED ARTIFICIAL MICROVESICLES BY USING CENTRIFUGAL FORCE

(71) Applicant: POSTECH ACADEMY—INDUSTRY FOUNDATION, Gyeongsangbuk-do (KR)

(72) Inventors: Jae-Sung Park, Gyeongsangbuk-do (KR); Wonju Jo, Busan (KR); Jun Ho Kim, Gyeongsangbuk-do (KR); Siwoo Cho, Gyeongsangbuk-do (KR); Hwapyeong Jeong, Chungcheongbuk-do (KR)

(73) Assignee: POSTECH ACADEMY-INDUSTRY FOUNDATION (KR)

( * ) Notice: Subject to any disclaimer, the term of this patent is extended or adjusted under 35 U.S.C. 154(b) by 230 days.

(21) Appl. No.: 14/781,071

(22) PCT Filed: Mar. 28, 2014

(86) PCT No.: PCT/KR2014/002699
§ 371 (c)(1),
(2) Date: Sep. 29, 2015

(87) PCT Pub. No.: WO2014/158005
PCT Pub. Date: Oct. 2, 2014

(65) Prior Publication Data
US 2016/0305857 A1 Oct. 20, 2016

(30) Foreign Application Priority Data
Mar. 29, 2013 (KR) .................. 10-2013-0034620

(51) Int. Cl.
*G01N 1/40* (2006.01)
*C12M 1/26* (2006.01)
*C12M 1/00* (2006.01)

(52) U.S. Cl.
CPC .......... *G01N 1/4077* (2013.01); *C12M 33/14* (2013.01); *C12M 47/06* (2013.01); *G01N 2001/4083* (2013.01); *G01N 2001/4088* (2013.01)

(58) Field of Classification Search
None
See application file for complete search history.

(56) References Cited

U.S. PATENT DOCUMENTS

2014/0212949 A1 7/2014 Kim et al.

FOREIGN PATENT DOCUMENTS

| EP | 2450032 A2 | 5/2012 |
|---|---|---|
| EP | 2617413 A2 | 7/2013 |
| JP | 4290916 B2 | 7/2009 |
| JP | 2011510663 A | 4/2011 |
| KR | 10-2001-0072638 A | 7/2001 |
| KR | 10-2011-0002443 A | 1/2011 |
| KR | 10-2012-0123624 A | 11/2012 |
| KR | 10-2013-0030846 A | 3/2013 |
| KR | 2013-0030846 A | 3/2013 |
| WO | 2011/063324 | 5/2011 |
| WO | 2011/063324 A2 | 5/2011 |
| WO | 2012/165815 A2 | 12/2012 |

OTHER PUBLICATIONS

Morton, Identifying Peptide Sensors for Highly Conserved Membranes and Lipid Components, Chemistry & Biochemistry Graduate Theses & Dissertations 97 (2013).*
Ming et al., 2011 "Erythrocyte membrane-camouflaged polymeric nanoparticles as a biomimetic delivery platform" PNAS, vol. 108, No. 27, pp. 10980-10985.
Zhu et al., 2013 "Vesicle extrusion through polycarbonate track-etched membranes using a hand-held mini-extruder", Methods Enzymol., vol. 533: 275-282.

* cited by examiner

*Primary Examiner* — Kortney L. Klinkel
*Assistant Examiner* — Stephen M Chong
(74) *Attorney, Agent, or Firm* — Riverside Law LLP

(57) ABSTRACT

The present invention relates to an apparatus for preparing cell-derived artificial microvesicles, and more specifically, to an apparatus for preparing artificial microvesicles by allowing cells, which are concentrated using centrifugal force, to pass through a porous filter. Artificial microvesicles prepared according to the present invention maintains the structure of the cell membrane as it is, and contains cytoplasm by minimizing the loss of cytoplasm by using a buffer solution during preparation. Therefore, the artificial microvesicles prepared using the apparatus of the present invention is expected to be useful for applied research such as the diagnosis of diseases, drug delivery techniques and basic research.

9 Claims, 6 Drawing Sheets

(a)

(b)

(a)                          (b)

(a)                          (b)

APPARATUS FOR PREPARING CELL-DERIVED ARTIFICIAL MICROVESICLES BY USING CENTRIFUGAL FORCE

CROSS-REFERENCE TO RELATED APPLICATIONS

This application is the U.S. national phase application filed under 35 U.S.C. § 371 claiming benefit to International Patent Application No. PCT/KR2014/002699, filed on Mar. 28, 2014, which is entitled to priority under 35 U.S.C. § 119(a)-(d) to Korea application no. 10-2013-0034620, filed Mar. 29, 2013, each of which application is hereby incorporated herein by reference in its entirety.

TECHNICAL FIELD

The present invention relates to an apparatus for preparing cell-derived artificial microvesicles, and more specifically, to an apparatus for efficiently preparing cell-derived artificial microvesicles using centrifugal force.

BACKGROUND ART

Microvesicles are a type of a cell organelle generally formed in the size of 0.03-1 um that are naturally released from a cell membrane in almost all cell types to be formed in a shape of a phospholipid bilayer and contain intracellular components such as messenger ribonucleic acid (mRNA), deoxyribonucleic acid (DNA), and protein.

As a basic tool of a cell for metabolism, transportation of a metabolic substance, storage of enzymes, chemical reactions, and the like, the microvesicles mediate intercellular signaling by delivering mRNA, microRNA (miRNA), and protein among cells. For example, microvesicles derived from a cancer cell induce changes in surrounding normal cells by delivering oncoprotein or miRNA. In addition, by being directly released from the cell membrane, the microvesicles hold an antigenic substance of a mother cell, thereby also being utilized in research for developing a vaccine. Besides, the microvesicles also play a role of removing misfolded protein, a cytotoxic substance or byproducts generated by intracellular metabolism.

Based on the intercellular signaling function of the microvesicles, a study has been actively carried out to develop a technology of delivering a drug or biomaterial to cells using an artificial phospholipid bilayer. The artificial microvesicles are widely utilized in biological experiments due to advantages of having high delivery efficiency and robustly protecting a substance to be delivered from an external environment.

However, artificial microvesicles prepared from the phospholipids purified from beans or eggs do not contain membrane protein, thus being unsuitable for inducing cell fusion. In addition, a process of removing the organic solvents is essential because surfactants and organic solvents used in preparing artificial microvesicls are toxic. Consequently, a method for preparing artificial microvesicles that are more serviceable in cell based experiments is required.

Recently, a technology of preparing artificial microvesicles by applying methods such as a conventional extrusion process or sonication process to a cell suspension to divide cells into small fragments and utilizing the artificial microvesicles in disease diagnosis or drug delivery has been disclosed (Title of Invention: Microvesicles derived from mammalian nucleated cell and use thereof, Inventor: GHO, Yong Song, Patent Application No. 10-2010-0063372). In addition, the inventors of the present invention have also developed a method of preparing artificial microvesicles from embryonic stem cells by a conventional extrusion method and treating somatic cells with the artificial microvesicles to induce the somatic cells to become induced pluripotent stem cells (Title of Invention: Method for preparing induced pluripotent stem cells using artificial microvesicles derived from embryonic stem cells, Inventor: PARK, Jae-Sung, Patent Application No. 10-2011-0040202).

In case of the preparing method mentioned above, the prepared artificial microvesicles mimic the structure of a cell membrane due to being derived from the cell membrane. However, a buffer solution etc. used during the preparation is included in the artificial microvesicles, causing cytoplasm itself to be diluted and a concentration of a target substance to be lowered as a result, thereby not only requiring a greater amount of artificial microvesicles to accurately diagnose a disease and deliver a predetermined amount of the target substance, but also having a problem of causing loss in an intracellular substance.

Accordingly, to solve the problems that may occur while preparing artificial microvesicles by conventional methods, the present inventors have developed an apparatus for preparing artificial microvesicles using centrifugal force, and completed the present invention by confirming that the artificial microvesicles prepared by the apparatus contain more intracellular components than the artificial microvesicles prepared by the conventional methods.

DISCLOSURE

Technical Problem

The present invention is directed to providing an apparatus for preparing cell-derived artificial microvesicles using centrifugal force, and a method of preparing cell-derived artificial microvesicles using the same.

However, the technical object of the present invention is not limited to that mentioned above, and other unmentioned objects will be clearly understood by those of ordinary skill in the art by descriptions below.

Technical Solution

According to the present invention, there is provided an apparatus for preparing cell-derived artificial microvesicles, the apparatus including: an injecting main body unit (100) configured to be injected with a cell suspension; a filter unit (200) connected to the injecting main body unit (100), and in which cells are crushed as the cell suspension is passed through; and a collecting main body unit (300) configured to collect artificial microvesicles formed by passing through the filter unit (200). The injecting main body unit (100) and the collecting main body unit (300) are formed symmetrical to the filter unit (200) to perform the same role and enable liquid to be passed through several times.

In addition, the present invention provide a method of preparing cell-derived artificial microvesicles using the apparatus, the method including: injecting a cell suspension into the apparatus; and preparing artificial microvesicles from the cells using centrifugal force. After the cells are injected into the injecting main body unit (100), the injecting main body unit (100) is inserted into a centrifuge as orientation of cell contained part should be upside, and rotated at a predetermined speed, causing a piston to descend by receiving centrifugal force. The piston pushes the cell suspension to enable the cells to pass through the filter. Cell-derived microvesicles are formed by a self-assembly characteristic of a cell membrane when the cells are crushed while passing through the filter.

According to an embodiment of the present invention, the injecting main body unit (100) may be formed by a lid (110), a piston (120), and a main body (130) sequentially connected to each other.

According to another embodiment of the present invention, the filter unit (200) may be formed by a filter (220) arranged to come in contact with the injecting main body unit (100) and positioned inside a filter support (230).

According to another embodiment of the present invention, the filter (220) may be positioned between two O-rings (210).

According to another embodiment of the present invention, the filter (220) may have a hole formed in the size of 0.2 to 30 μm.

According to another embodiment of the present invention, the filter (220) may be formed of a polycarbonate material.

According to another embodiment of the present invention, the filter support (230) may have a hole (231) formed in the size of 0.1 to 2 mm.

According to another embodiment of the present invention, the collecting main body unit (300) may be formed by a main body (330), a piston (320), and a lid (310) sequentially connected to the filter unit (200).

According to another embodiment of the present invention, one O-ring (210) may be positioned between the filter support (230) and the collecting main body unit (300).

Advantageous Effects

According to the present invention, an apparatus for preparing cell-derived artificial microvesicles prepares microvesicles by allowing cells, which are concentrated using centrifugal force, to pass through a porous filter, thereby not only maintaining the structure of the cell membrane as it is, but also minimizing loss of cytoplasm by a buffer solution used during the preparation. Consequently, the apparatus of the present invention not only can efficiently prepare a great amount of cell-derived artificial microvesicles, but also can be widely utilized in basic research using the prepared microvesicles and technologies related to disease diagnosis and drug delivery.

MODES OF THE INVENTION

Hereinafter, the present invention will be described in detail.

Figure 1:
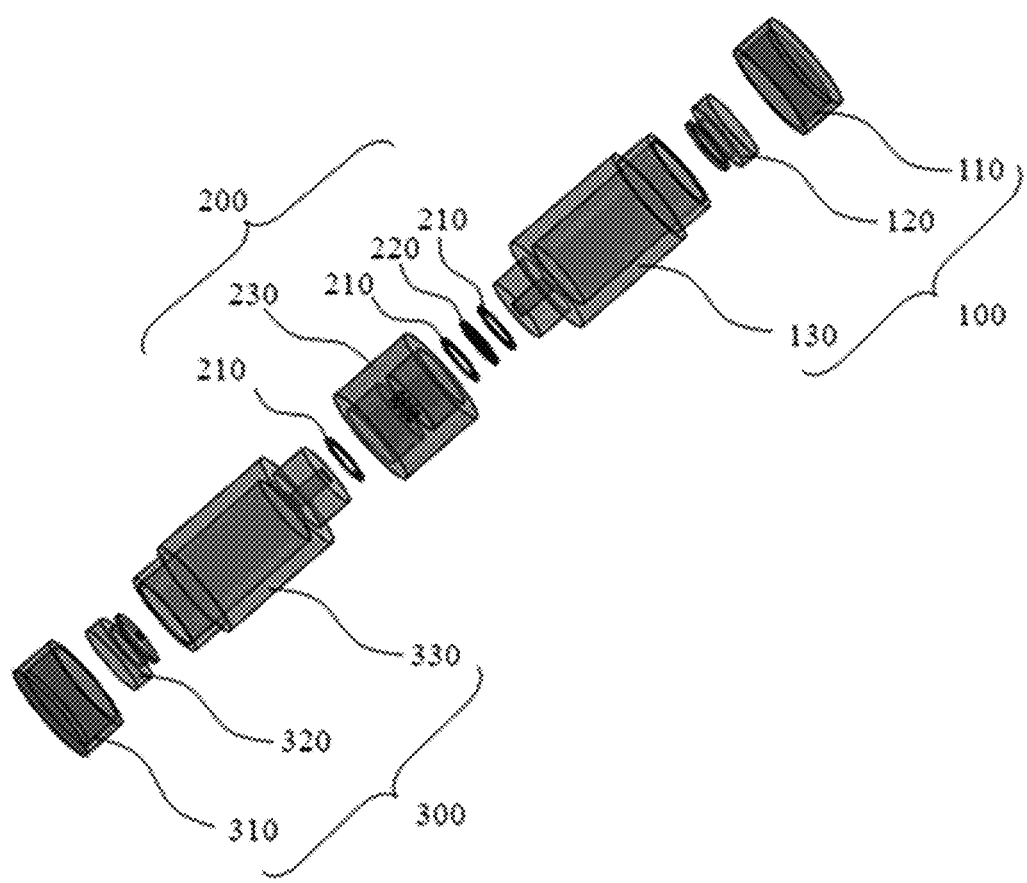
FIG. 1 is an overall structural drawing of an apparatus provided by the present invention.

According to the present invention, that provide an apparatus for preparing cell-derived artificial microvesicles, the apparatus including: an injecting main body unit 100 configured to be injected with a cell suspension; a filter unit 200 in which cells are crushed as the cell suspension is passed through; and a collecting main body unit 300 configured to accommodate artificial microvesicles formed by passing through the filter unit 200 (see FIG. 1).

Nucleated cells of mammals or transformed cells thereof may be used as the cells above, but any cell capable of preparing artificial microvesicles through the apparatus may be used. The transformed cells may be a specific protein, a targeting molecule, a cell transformed to express a substance required for cell membrane fusion with a target cell, and a transformed cell formed of a combination of two or more of the above, but are not limited thereto.

In addition, layers of the artificial microvesicles may further include other components besides cell membranes of the cells. Specifically, the components besides the cell membranes may include a targeting molecule, a fusogen, cyclodextrin, polyethylene glycol, etc., may be added by various methods, and include a chemical modification of the cell membranes, but are not limited thereto.

According to an embodiment of the present invention, artificial microvesicles were prepared using a HeLa cell obtained from a cervical cancer tissue (see Embodiment 1).

The injecting main body unit (100) is formed by a lid (110), a piston (120), and a main body (130) sequentially connected to each other. The main body (130) is a space for accommodating a cell suspension, and when centrifugal force is applied, the piston (120) pushes the cell suspension in the main body (130) toward the filter unit (200). Here, an outer diameter of the piston and an inner diameter of the main body are equal to each other so that, when injecting the cell suspension into the main body, the cells are not leaked and a part for sealing may be added to fill a slight gap between the piston and the main body.

The filter unit (200) is formed by a filter (220) arranged to come in contact with the injecting main body unit and positioned inside a filter support (230). Here, the filter is positioned to come in contact with the injecting main body unit, and when centrifugal force is applied, the cell suspension is crushed while passing through the filter. It is preferable that a hole of the filter (220) be formed in the size of 0.2 to 30 μm, but the size is not limited thereto. In addition, in general, the material of the filter may be a hydrophobic substance capable of having water passed therethrough, such as metal, polymer, glass, silicon, etc. and is preferably a polycarbonate material, but any material that can be processed in the size of the hole and does not change physico-chemical properties of cells may be used.

O-rings (210) are respectively arranged at both sides of the filter (220) for sealing, and an O-ring (210) is also arranged at the other surface of the filter support (230) where the filter (220) is not arranged. Here, a supporting membrane of a mesh structure may be arranged between the filter and the O-rings to support the filter.

Figure 2:
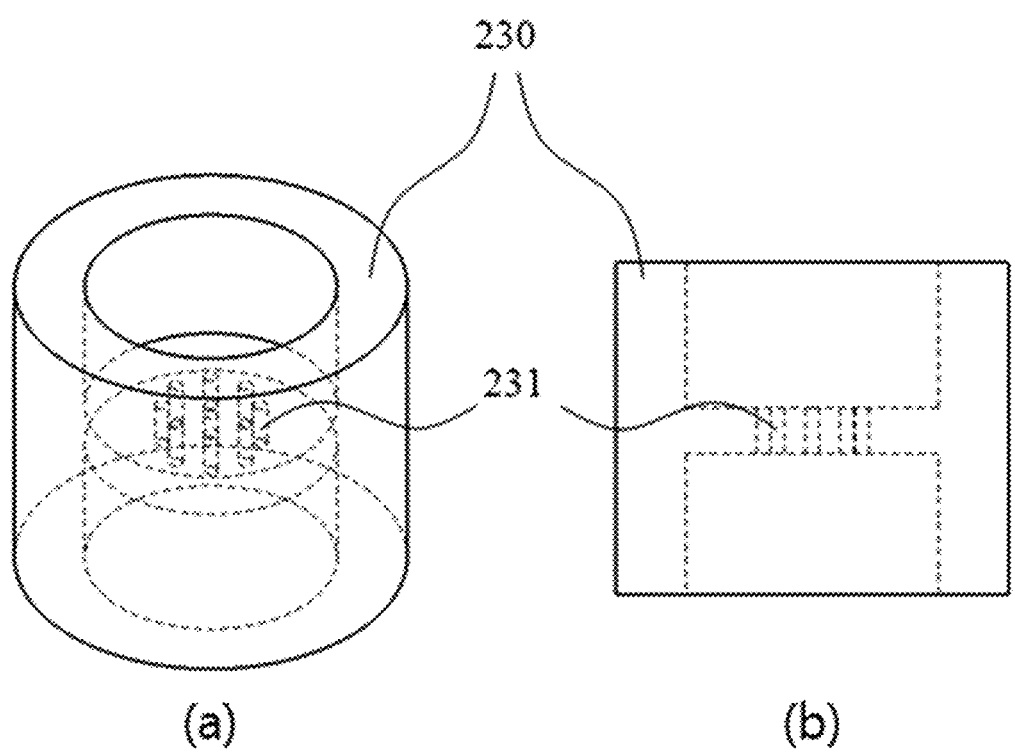
FIG. 2 is an enlarged drawing (a) and a cross-sectional view (b) of a filter support shown in FIG. 1.
Figure 3:
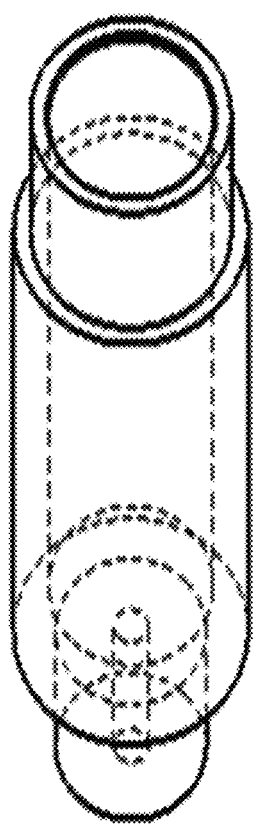
FIG. 3 is an enlarged drawing (a) and a cross-sectional view (b) of a main body shown in FIG. 1.
Figure 3:
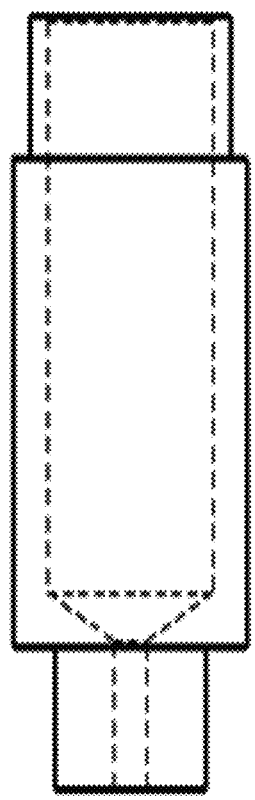
Figure 4:
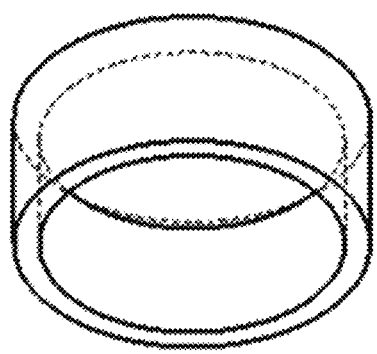
FIG. 4 is an enlarged drawing (a) and a cross-sectional view (b) of a lid shown in FIG. 1.
Figure 4:
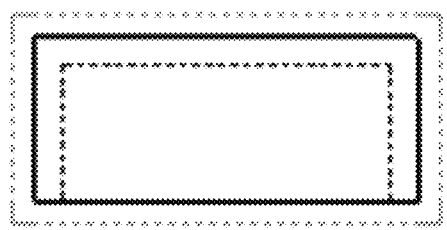
Figure 5:
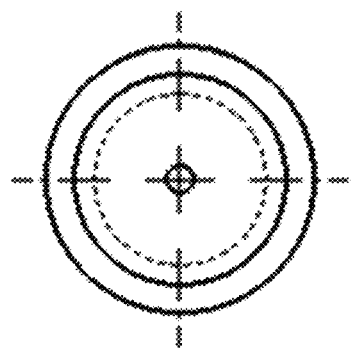
FIG. 5 is an enlarged drawing (a) and a cross-sectional view (b) of a piston shown in FIG. 1.
Figure 5:

The filter support (230) supports the filter, and both side surfaces thereof are connected to the injecting main body unit (100) and the collecting main body unit (300), respectively. Here, each of the main bodies (130 and 330) are connected to the filter support using screw threads, and a sealing part may be added to fill a slight gap, but the connection is possible by any known common methods in the art. In addition, the filter support may have a hole formed in the size of 0.1 to 2 mm so that the cell suspension crushed by the filter can pass therethrough, but the size is not limited thereto (see FIG. 2).

The collecting main body unit (300) is a space for collecting the cell suspension crushed while passing the filter support (230), and is formed by a main body (330), a piston (320), and a lid (310) sequentially connected to the filter unit (200).

The injecting main body unit (100) and the collecting main body unit (300) are formed symmetrical to each other to enable cells to pass through the filter several times. The cell suspension passed from the injecting main body unit to the collecting main body unit can be returned to the injecting main body unit from the collecting main body unit by receiving centrifugal force. Here, the roles of the injecting main body unit and the collecting main body unit are changed. That is, the main body (330) of the collecting main body unit (300) is a space for collecting the cell suspension, and when centrifugal force is applied, the piston (320) pushes the cell suspension in the main body toward the filter unit (200).

According to the present invention, an inlet of the main body of the injecting main body unit is formed in a way that an inlet of a syringe can be inserted the inlet, thereby injecting the cell suspension at one time with the syringe. In addition, each of the main bodies (130 and 330) of the injecting main body unit and the collecting main body unit are connected to be symmetrical to both sides with respect to the filter support (230) to accommodate the cell suspension and suspension passed through the filter, respectively, thereby being arranged to enable the cells to pass through the filter several times.

The artificial microvesicles prepared by the apparatus are divided into an inner portion and an outer portion by phospholipid bilayers formed of cell membrane components of cells from which the artificial microvesicles are derived, contain cell membrane lipids, cell membrane protein, nucleic acid, and cellular components etc. of the cells from which the artificial microvesicles are derived, and are smaller than original cells, but are not limited thereto.

In addition, according to the present invention, there is provided a method of preparing cell-derived artificial microvesicles using the apparatus, the method including: injecting cells into the apparatus; and preparing artificial microvesicles from the cells using centrifugal force.

The centrifugal force applied in the method may be provided using a centrifuge, and it is preferable that the size of the centrifugal force be in a range of 1,000 to 2,000 g and the time duration of operating the centrifuge be in a range of 1 to 3 minutes, but the size and the time duration are not limited thereto. In addition, the centrifugal method can be repeatedly performed to prepare artificial microvesicles of uniform size, and preferably, the cell suspension can repeatedly pass through the filter two to five times, but the number of times is not limited thereto.

Hereinafter, exemplary embodiments are provided to assist in understanding of the present invention. However, the embodiments below are only provided to make the present invention easier to understand, and the content of the present invention is not limited by the embodiments below.

Embodiment 1. Preparation of Artificial Microvesicles Using the Apparatus According to the Present Invention 1-1. Forming Artificial Microvesicles Using the Apparatus According to the Present Invention First, a polycarbonate filter having a 10 μm hole was inserted into the filter support (230). Then, the filter support (230) was assembled to the main body (130), alcohol was passed through several times for washing, and a phosphate buffered saline (PBS) solution was passed through for washing. The HeLa cell obtained from a cervical cancer tissue was resuspended in 1 ml of the PBS solution at the concentration of $5 \times 10^7$ cells/ml. After injecting the suspension into the main body, the main body was loaded into a centrifuge, the centrifuge was operated at 1,300 g for one minute and forty-five seconds, and the operation was repeated three times. A polycarbonate filter with a 5 μm hole was inserted into and assembled to a separate filter support, and washing with alcohol and the PBS solution was performed as in the process above. The HeLa cell passed through the polycarbonate filter with a 10 μm hole was inserted into the main body again, the centrifuge was operated at 1,300 g for one minute and forty-five seconds, and the operation was repeated three times.

1-2. Obtaining Artificial Microvesicles

In an ultracentrifuge tube of 2.2 ml volume, a 50% OptiPrep solution 400 μl, a 10% OptiPrep solution 600 μl, and 1 ml of suspension passed through the polycarbonate filter with a 5 μm hole prepared in the embodiment 1-1 were sequentially placed. Then, ultracentrifugation took place for an hour at 100,000 g. Here, artificial microvesicles were finally obtained from a layer between the 50% OptiPrep solution and the 10% OptiPrep solution formed after the centrifugation.

Embodiment 2. Characteristic Analysis of Artificial Microvesicles

The artificial microvesicles prepared from the HeLa cell in accordance with the method of Embodiment 1 were adsorbed onto a glow-discharged carbon-coated copper grid for three minutes. After washing the grid with distilled water, the grid was stained with 2% uranylacetate for a minute and was observed by a transmission electron microscope JEM101 (Jeol, Japan).

Figure 6:
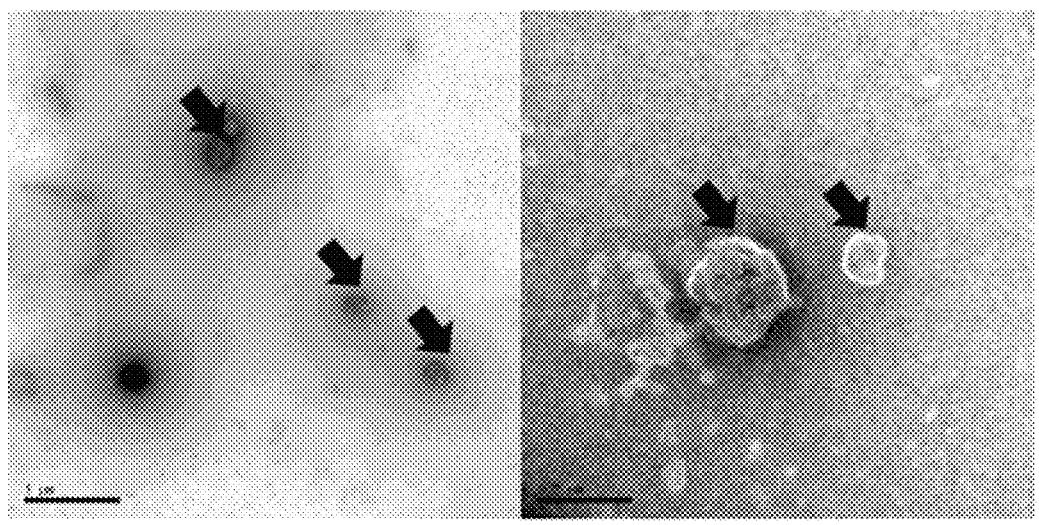
FIG. 6 is a transmission electron microscopy image of artificial microvesicles prepared in the present invention.

As shown in FIG. 6, it was found that the artificial microvesicles prepared from the HeLa cell are formed of phospholipid bilayers, are formed in the size of 100-200 nm, and are mostly formed in a spherical shape.

Figure 7:
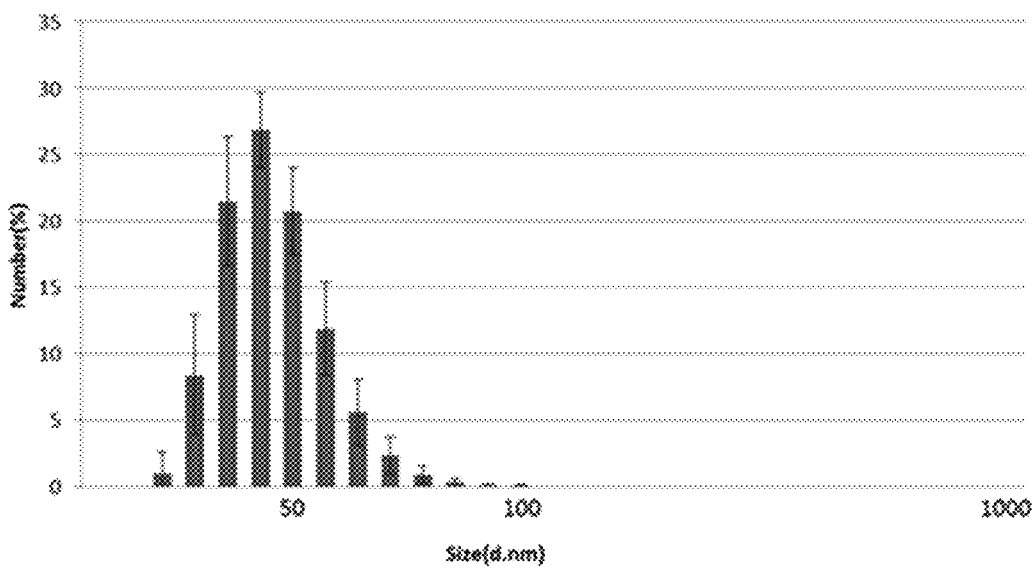
FIG. 7 is a graph showing the size of artificial microvesicles prepared in the present invention.

To check the size of the artificial microvesicles, the artificial microvesicles were diluted in 1 ml of the PBS solution to the concentration of 5 μg/ml, were inserted into a cuvette, were analyzed by a dynamic light-scattering, and the result is shown in FIG. 7.

As shown in FIG. 7, it was confirmed that the size of the artificial microvesicles ranges from 25-100 nm, and the average size is about 50 nm.

Embodiment 3. Comparative Analysis of Cytoplasm in Artificial Microvesicles

A comparative analysis was done on cytoplasmic components in the artificial microvesicles prepared by the apparatus according to the present invention and the artificial microvesicles prepared by a commercialized extruder. First, artificial microvesicles prepared from the HeLa cell in accordance with the method of Embodiment 1 were prepared.

To use the commercialized extruder, the HeLa cell was resuspended in 1 ml of the PBS solution at the concentration of $5 \times 10^7$ cells/ml, the suspension was passed through the polycarbonate filter with a 10 µm hole three times using a mini extruder, Avanti, and was again passed through the polycarbonate filter with a 5 µm hole three times. In the ultracentrifuge tube of 2.2 ml volume, a 50% OptiPrep solution 400 µl, a 10% OptiPrep solution 600 µl, and 1 ml of the suspension passed through the polycarbonate filter with a 5 µm hole were sequentially placed. Then, ultracentrifugation took place for an hour at 100,000 g. Artificial microvesicles were obtained from a layer between the 50% OptiPrep solution and the 10% OptiPrep solution formed by the ultracentrifugation.

3-1. Checking the Amount of RNA

To compare the amount of RNA existing in the artificial microvesicles prepared by each of the methods, the amount of protein was measured using a BCA protein assay Kit (Thermo scientific), and RNA was separated with respect to 200 µg of protein. After adding 0.6 ml of Trizol (Life Technologies) to each of the samples, layers of the artificial microvesicles were dissolved for five minutes. Next, 0.2 ml of a chloroform solution was added and mixed well, and an RNA layer was separated from layers of other substances (protein, DNA) for five minutes at 4° C. After dividing the layers by centrifugation at 13,500 g for ten minutes, the separated upper layer (RNA layer) was separately transferred, and isopropyl alcohol (IPA) of the same volume was added to precipitate RNA for twenty minutes at −20° C. To completely precipitate the RNA, centrifugation at 13,500 g took place for ten minutes to precipitate the RNA, and the supernatant was removed. After adding 75% ethanol to the precipitate, centrifugation at 13,500 g took place for ten minutes to completely remove the ethanol, and the precipitate was dried under a room temperature for five minutes or longer. The dried substance was dissolved by adding DI water, and the amount of RNA was measured using a spectrophotometer (Genova) (FIG. 8).

Figure 8:
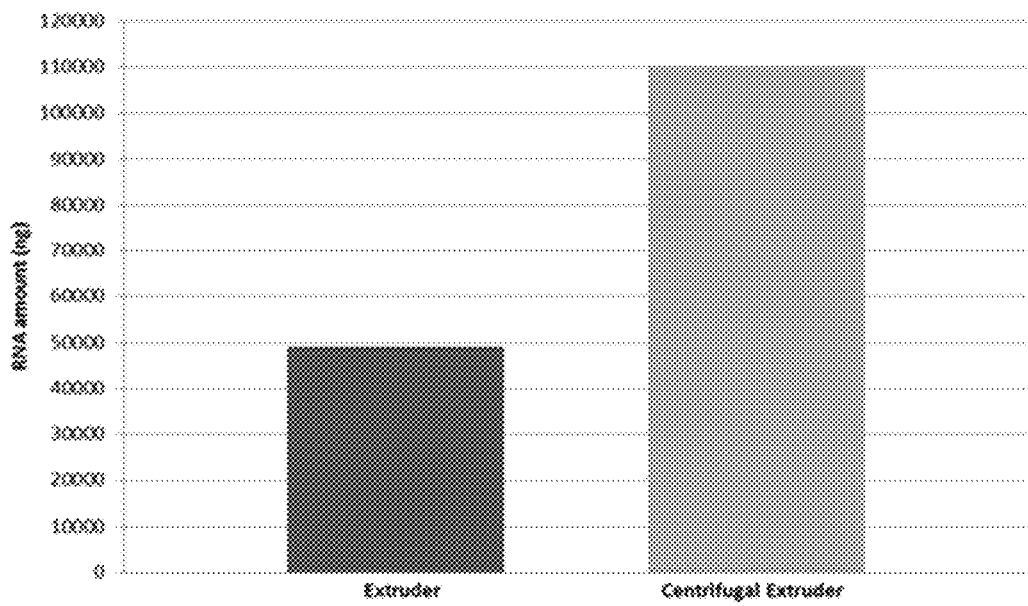
FIG. 8 is a graph comparing the amount of RNA contained in artificial microvesicles prepared using a commercialized extruder and artificial microvesicles prepared in the present invention (the artificial microvesicles prepared by the commercialized extruder are marked as "Extruder", while the artificial microvesicles prepared in the present invention are marked as "Centrifugal Extruder").

As shown in FIG. 8, it was confirmed that, compared with the artificial microvesicles (Extruder) prepared using the mini extruder, Avanti, the artificial microvesicles (Centrifugal Extruder) prepared by the method of Embodiment 1 contain at least twice as much RNA.

3-2. Checking the Amount of Protein

In addition, to compare the amount of protein existing in the artificial microvesicles prepared by each of the methods, the amount of protein was measured using a BCA protein assay kit (Thermo scientific), and layers of the artificial microvesicles were decomposed using 2% Trion X-100 (Sigma) with respect to 200 µg of protein. To separate phospholipids, centrifugation at 10,000 g took place for ten minutes to precipitate the phospholipids, and the separated upper layer was measured using the BCA protein assay kit (Thermo scientific) (FIG. 9).

Figure 9:
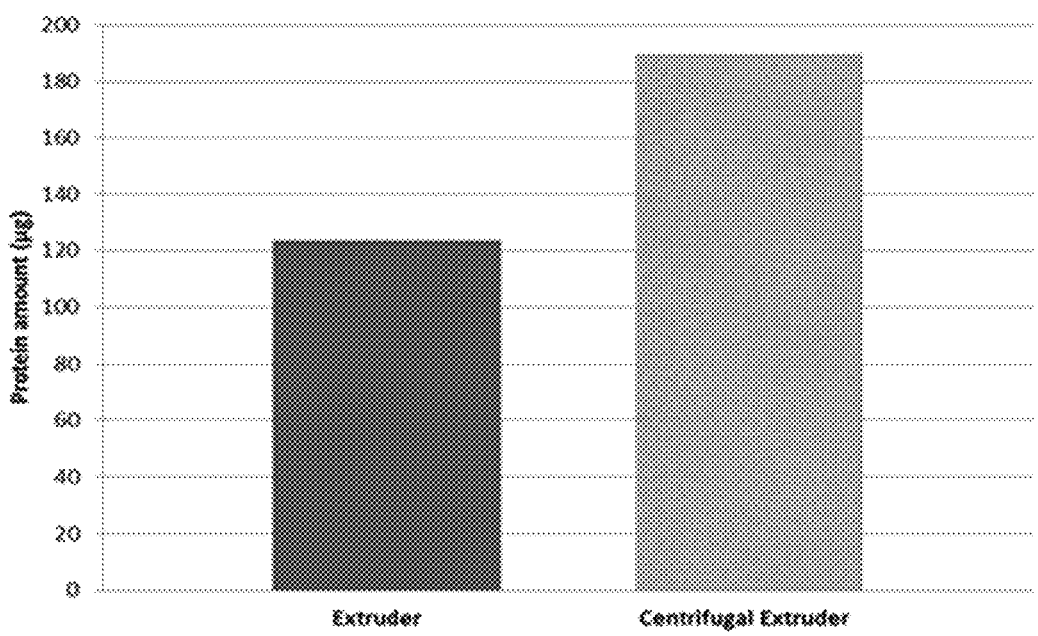
FIG. 9 is a graph comparing the amount of protein contained in the artificial microvesicles prepared using the commercialized extruder and the artificial microvesicles prepared in the present invention.

As shown in FIG. 9, it was found that, compared with the artificial microvesicles prepared using the mini extruder, Avanti, the cell-derived artificial microvesicles prepared by the method of Embodiment 1 contain at least twice as much protein.

The aforementioned descriptions of the present invention are for illustrative purposes, and those of ordinary skill in the art will understand that the present invention can be easily changed into other specific forms without changing the technical spirit or essential features of the present invention. Therefore, the embodiments mentioned above should be construed as being illustrative in all aspects, and non-limiting.

DESCRIPTION OF REFERENCE NUMERALS

100: Injecting main body unit
110: Lid
120: Piston
130: Main body
200: Filter unit
210: O-ring
220: Filter
230: Filter support
231: Hole of filter support
300: Collecting main body unit
310: Lid
320: Piston
330: Main body

INDUSTRIAL APPLICABILITY

According to the present invention, an apparatus for preparing cell-derived artificial microvesicles allows cells, which are concentrated using centrifugal force, to pass through a porous filter so that the microvesicles prepared by the apparatus not only maintain the structure of the cell membrane as it is but also contain cytoplasm by minimizing loss of cytoplasm. Consequently, problems of microvesicles prepared by an existing apparatus related to a difficulty of inducing cell fusion and a need for removing surfactants and organic solvents being used can be overcome.

The microvesicles prepared using the apparatus according to the present invention not only can be used in basic research, but also can be useful for applied research such as technologies related to disease diagnosis and drug delivery.

The invention claimed is:
1. A method of preparing cell-derived artificial microvesicles, the method comprising:
   injecting a cell suspension into an apparatus for preparing cell-derived artificial microvesicles,
   the apparatus comprising an injecting main body unit (100) formed by a lid (110), a piston (120), and a main body (130) sequentially connected to each other; a filter unit (200) connected to the injecting main body unit (100); and a collecting main body unit (300) connected to the filter unit (200);
   crushing cells by using the piston (120) to pass the cell suspension in the injecting main body unit (100) through the filter unit (200) by centrifugal force; and
   collecting self-assembled artificial microvesicles formed by the crushed cells passing through the filter unit (200) in the main body unit (300).

2. The method of claim 1, wherein the filter unit (200) is formed by a filter (220) arranged to come in contact with the injecting main body unit (100) and positioned inside a filter support (230).

3. The method of claim 2, wherein the filter (220) is positioned between two O-rings (210).

4. The method of claim 2, wherein the filter (220) has a hole formed in the diameter of 0.2 to 30 µm.

5. The method of claim 2, wherein the filter (220) is formed of a polycarbonate material.

6. The method of claim 2, wherein the filter support (230) has a hole (231) formed in the diameter of 0.1 to 2 mm.

7. The method of claim 1, wherein the collecting main body unit (300) is formed by a main body (330), a piston (320), and a lid (310) sequentially connected to the filter unit (200).

8. The method of claim 1, wherein one O-ring (210) is positioned between the filter support (230) and the collecting main body unit (300).

9. The method of claim 1, wherein the artificial microvesicles retain a component of the crushed cells selected from the group consisting of: cell membrane lipids, cell membrane proteins, nucleic acids, cytoplasm, and combinations thereof.

* * * * *